US006761562B2

United States Patent
Von Weissenfluh

(10) Patent No.: US 6,761,562 B2
(45) Date of Patent: Jul. 13, 2004

(54) INTERDENTAL WEDGE

(75) Inventor: Beat A. Von Weissenfluh, Gentilino (CH)

(73) Assignee: KerrHawe SA (CH)

( * ) Notice: Subject to any disclaimer, the term of this patent is extended or adjusted under 35 U.S.C. 154(b) by 0 days.

(21) Appl. No.: 10/132,644

(22) Filed: Apr. 25, 2002

(65) Prior Publication Data

US 2003/0113688 A1 Jun. 19, 2003

(Under 37 CFR 1.47)

Related U.S. Application Data

(63) Continuation of application No. 09/964,220, filed on Sep. 26, 2001, now abandoned.

(30) Foreign Application Priority Data

Sep. 29, 2000 (CH) .............................. 1916/00

(51) Int. Cl.⁷ ................................ A61C 3/00
(52) U.S. Cl. .................................... 433/149
(58) Field of Search .................. 433/149, 80, 39, 433/148, 136, 141, 139, 229, 72; 132/321, 329

(56) References Cited

U.S. PATENT DOCUMENTS

| 3,815,243 | A | * | 6/1974 | Eames ......................... 433/149 |
| 5,527,181 | A | * | 6/1996 | Rawls et al. ................. 433/149 |
| 5,743,738 | A | | 4/1998 | Baffelli et al. .............. 433/149 |
| 6,220,858 | B1 | * | 4/2001 | McKenna et al. ............ 433/39 |

* cited by examiner

Primary Examiner—Kevin Shaver
Assistant Examiner—Melba Bumgarner
(74) Attorney, Agent, or Firm—Wood, Herron & Evans, LLP

(57) ABSTRACT

The interdental wedge is particularly intended for use in the insertion of approximal fillings of light-curing synthetic materials and consists of a combination of a wedge body and an underlying compressible sole comprising a rim which projects on both sides of the wedge body. The sole portion is preferably made of a thermoplastic elastomer and the wedge body of a translucent synthetic material. A wedge of this kind provides a strong spreading force, and the two rims are deformed when inserted, thereby ensuring a firm retention and a tight application of the matrix to the dental anatomy, and they form sealing lips in order to keep away the saliva from the treated area and to gently displace the papilla.

10 Claims, 1 Drawing Sheet

INTERDENTAL WEDGE

This application is a continuation of application Ser. No. 09/964,220 filed Sep. 26, 2001, now abandoned.

FIELD OF THE INVENTION

The present invention refers to an interdental wedge, particularly for use in the insertion of approximal fillings of light curing synthetic materials, composed of a combination of a wedge body and of an underlying compressible sole portion.

BRIEF DESCRIPTION OF THE PRIOR ART

An interdental wedge of this kind is known from U.S. Pat. No. 5,743,738 to the applicant of the present invention. This prior art interdental wedge is essentially composed of a compressible sole portion of an elastomeric material and of an insert of a preferably light-conducting material with means allowing to conduct the light to the synthetic filling to be cured. In the application of this interdental wedge, which offered significant advantages over the prior art of the time, it has been found that this wedge is capable of being further improved. In particular, it has been found that it would be desirable to protect the treated area from penetrating sulcus liquids and to provide a better adaptation of the matrix to the dental anatomy under the approximal shoulder in the approximal space.

SUMMARY OF THE INVENTION

On the background of this prior art, it is the object of the present invention to provide an interdental wedge offering an improved retention, on one hand, as well as an improved sealing of the treated area and a better adaptation of the matrix to the dental anatomy under the approximal shoulder in the approximal space. This object is attained by an interdental wedge wherein the sole portion comprises a rim projecting on both sides of the wedge body. Further improvements and details are described in the dependent claims. An effective and easily manufacturable identification means of different wedge types is indicated in dependent claim 6.

BRIEF DESCRIPTION OF THE DRAWINGS

The invention is explained in more detail hereinafter with reference to drawings of an exemplary embodiment.

DETAILED DESCRIPTION OF THE INVENTION

Wedge 1 is essentially composed of a wedge body 2 and of a sole portion 3 of a thermoplastic elastomer. If the wedge is used in the preferred field of application, i.e. for light-curing synthetic fillings, the wedge body is made of a translucent synthetic material. In contrast to the U.S. Patent Application cited in the introduction, sole portion 3 is not made of wood but of a thermoplastic elastomer.

The use of a thermoplastic elastomer, e.g. of the ELVAX product line of Dupont de Nemours, Switzerland, offers the advantage that sole portion 3 including rims 4 and the inner prism 5 can be formed in one piece and that this material may be colored by means of a clinically safe light-diffusing substance such as e.g. titanium dioxide in order to serve as a reflector.

Figure 1:
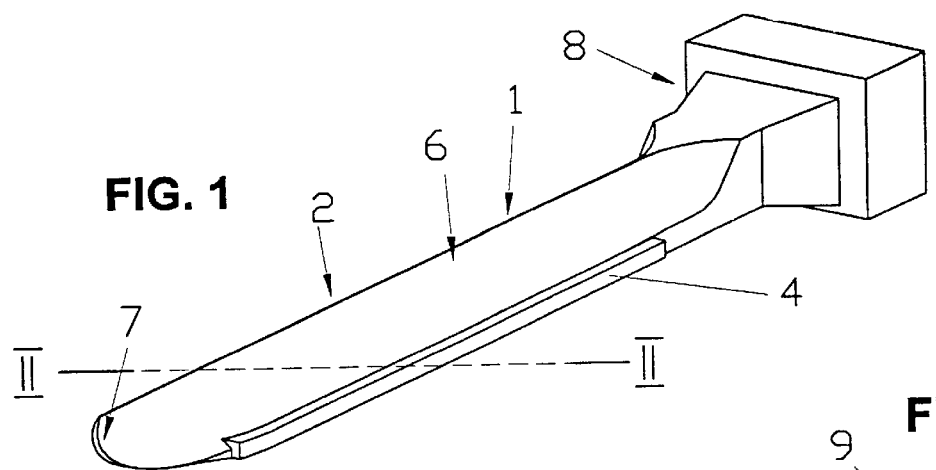
FIG. 1 shows the interdental wedge of the invention in a perspective view.

Wedge body 2 of FIG. 1 essentially consists of a V-shaped portion 6, a rounded tip 7 and, at the end opposite the tip, of an entry portion having a front side 8, and it is made of a translucent synthetic material which is basically known from the patent application mentioned in the introduction and from commercially available light-conducting wedges. Furthermore, rounded tip 7 is curved as it is known from other wedges. In order to reduce the risk of injuries, upper edge 9 is rounded as well, see FIG. 2.

If the light-conducting properties are not necessary while the good adhesive and separating properties are desired, as mentioned before, the sole portion including the rims may be made of wood and need not comprise the inner prism 5, and the corresponding portion of the wedge body need not necessarily be V-shaped in this case.

The parallelepipedic front section 8 of the wedge body is designed to receive the light emitted by an apparatus known per se and to transmit it through the V-shaped portion, the light emanating from the bottom of the V-shaped portion being reflected by the inner prism 5, such that instead of being lost, this portion of the light is effective in the light curing of the synthetic filling. Transparent thermoplastic synthetic resins such as acrylic resins, polycarbonates, PMMA or similar synthetic materials have been found to be the most suitable materials for the wedge body.

Figure 2:
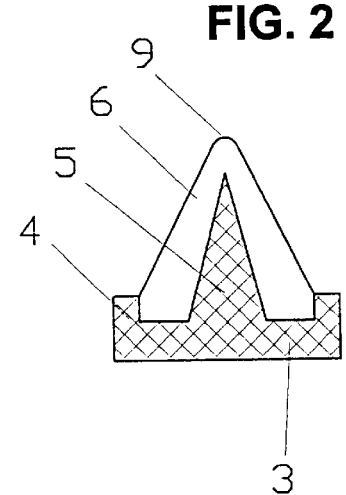
FIG. 2 shows a cross-section according to line II-II in FIG. 1.

FIG. 2 further illustrates that when compressed, V-shaped portion 6 develops a spring effect, whereas inner prism 5, being made of a thermoplastic elastomer, is slightly compressed and serves as a buffer. This combination of an elastomeric sole portion and of the V-shaped wedge body portion results in a specially firm retention of the wedge and in a very good separation of the teeth.

Figure 3:
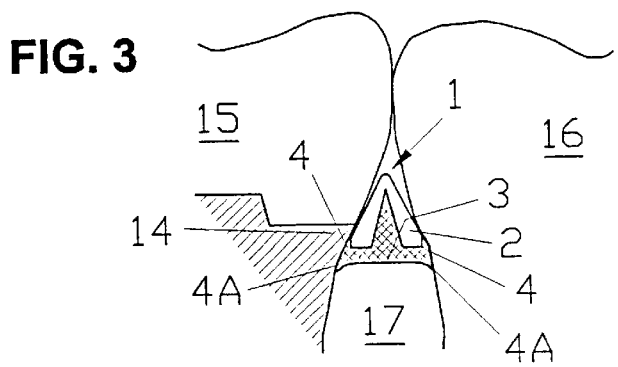
FIG. 3 schematically shows the sealing action of the interdental wedge of FIG. 1 when inserted.

FIG. 3 illustrates that the two rims 4 provide a close fit in the approximal zone, i.e. below the approximal shoulder 14 of teeth 15 and 16, and form sealing lips 4A extending downwards towards the gums which gently displace papilla 17.

The manufacture of the interdental wedge of the invention can be effected according the two-component process in a single injection mold by first injecting the sole portion from a thermoplastic elastomer and subsequently molding the wedge body from a translucent synthetic resin on top of the sole portion.

Alternatively, it is also possible to manufacture the sole portion and the wedge body separately and to assemble them by ultrasonic welding, friction welding or by a suitable adhesive. This is particularly appropriate in those cases where no light conduction is necessary and the two portions, i.e. the sole portion of wood, or of a synthetic material having similar properties, and the wedge body are separately manufactured and subsequently assembled.

The curve representing the deformation of the sole portion under the action of a force is the same as in the cited U.S. patent application and illustrated in FIG. 9 of the latter, i.e. the force opposing a deformation increases quickly, such that the increase of the compressive force is superproportional to the increase of the compression. According to the patent mentioned in the introduction, a great number of thermoplastic elastomers are known, particularly with compressible bodies having suitable properties and mainly a sufficient deformability for the rims to form sealing lips which keep the sulcus liquids from penetrating into the area of treatment while simultaneously pressing on the matrix below the approximal shoulder.

The preceding description shows that the wedge of the invention perfectly fulfills the requirements with respect such wedges. The wedge of FIG. 1 provides a) a firm retention, b) a tight seal of the treated area against the sulcus liquids, c) a close adaptation of the matrix to the contours of the teeth, and d) an effective separation of the teeth.

Figure 4:
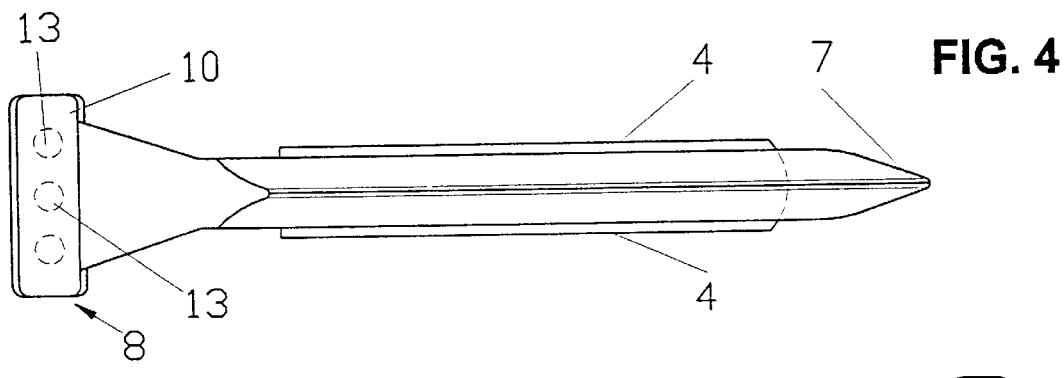
FIG. 4 shows a bottom view of the interdental wedge of FIG. 1.
Figure 5:
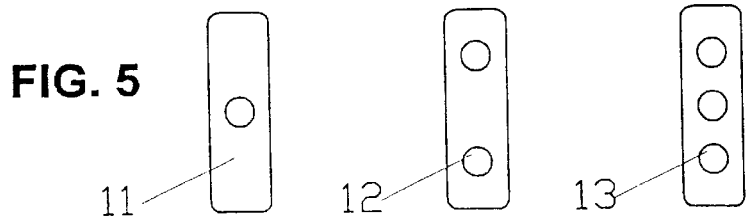
FIG. 5 shows details of the wedge of FIG. 4.

For the treatment of different teeth and for different patients, different sizes of wedges are required, and according to the prior art, the latter are generally marked by means of colorations or the like for distinction. Now, according to FIGS. 3 and 4, the underside 10 of the parallelepipedic front section 8, see FIG. 4, is provided with marks, e.g. one indentation 11, two indentations 12 or three indentations 13. Such a mark may be produced in the course of the manufacture of the wedge body, so that additional colorations or special aftertreatments of the kind are no longer necessary.

Since the body in which the marks are provided is relatively thick, if they are deep enough, the indentations will be more translucent than the body, thereby forming luminous spots which are easy to locate and to interprete.

It is understood that other marks such as bars or triangles and the like may provided instead of circular indentations, and that a smaller or a greater number of marks may be provided according to the type of wedge. Alternatively, projecting marks may be provided which are also palpable.

What is claimed is:

1. An interdental wedge, particularly for use in the insertion of approximal fillings of light-curing synthetic materials, comprising:

a wedge body; and an underlying compressible sole portion, said sole portion including a pair of elongate, longitudinally extending rims disposed along opposite sides of said sole portion;

said wedge body and at least a part of said sole portion defining a generally triangular shape having adjacent upper sides lying substantially in respective intersecting planes, said planes intersecting along a line parallel to a longitudinal direction of said wedge body;

said rims extending from said sole portion, on opposite sides of said wedge body, laterally outward from said intersecting planes.

2. The interdental wedge of claim 1, wherein said sole portion consists of a material which, from the uncompressed state, is compressible by a force which on further compression increases superproportionally with respect to the compression.

3. The interdental wedge of claim 1, wherein said sole portion is manufactured from a thermoplastic elastomer containing a light-diffusing substance, and wherein said wedge body is manufactured from a translucent synthetic material.

4. The interdental wedge of claim 1, wherein said sole portion comprises an inner prism, said wedge body having a corresponding portion which has a V-shaped design.

5. The interdental wedge of claim 4, wherein said wedge body comprises an entry portion having a front section allowing to collect the light impinging thereon and to conduct it to the inclined surfaces of the inner prism.

6. The interdental wedge of claim 5, wherein one side of said entry portion is provided with marks in order to identify the wedge size or its properties.

7. The interdental wedge of claim 6, wherein said marks consist of a number of indentations having a depth such that they are more translucent than the entry portion in which they are located.

8. The interdental wedge of claim 1, wherein said rims are configured to form a liquid impermeable seal between the interdental wedge and a patient's dental anatomy when installed in a patient's mouth.

9. The interdental wedge of claim 1, wherein said rims extend outward from said wedge body at a distance spaced from a tip of the interdental wedge.

10. A method of treating a tooth using an interdental wedge of claim 1, the method comprising:

inserting the interdental wedge in the area between the tooth to be treated and an adjacent tooth;

deforming the rims;

displacing the patient's gum with the deformed rims; and forming a liquid impermeable seal with the deformed rims, between the interdental wedge and the tooth to be treated.

* * * * *